United States Patent
Barcikowski et al.

(10) Patent No.: US 9,097,709 B2
(45) Date of Patent: Aug. 4, 2015

(54) METHOD AND DEVICE FOR PRODUCING METAL-CONTAINING ORGANIC COMPOUNDS

(75) Inventors: Stephan Barcikowski, Hannover (DE); Svea Petersen, Rostock (DE)

(73) Assignee: Laser Zentrum Hannover, e.V., Hannover (DE)

( * ) Notice: Subject to any disclaimer, the term of this patent is extended or adjusted under 35 U.S.C. 154(b) by 843 days.

(21) Appl. No.: 13/003,720

(22) PCT Filed: Jul. 15, 2009

(86) PCT No.: PCT/EP2009/059116
§ 371 (c)(1),
(2), (4) Date: Apr. 4, 2011

(87) PCT Pub. No.: WO2010/007117
PCT Pub. Date: Jan. 21, 2010

(65) Prior Publication Data
US 2011/0189695 A1    Aug. 4, 2011

(30) Foreign Application Priority Data

Jul. 15, 2008 (DE) ............................. 102008033070
Jul. 17, 2008 (DE) ............................. 102008033570

(51) Int. Cl.
*G01N 33/532* (2006.01)
*G01N 33/543* (2006.01)
*C12N 5/071* (2010.01)

(52) U.S. Cl.
CPC ............ *G01N 33/532* (2013.01); *C12N 5/0612* (2013.01); *G01N 33/54313* (2013.01); *G01N 33/54346* (2013.01)

(58) Field of Classification Search
USPC ................. 435/6, 286.7, 287.2, 287.3, 288.3; 436/518, 523, 525, 538; 422/402, 417, 422/504, 505
See application file for complete search history.

(56) References Cited

U.S. PATENT DOCUMENTS 7,563,318 B1 * 7/2009 Faucher et al. ............... 106/496
8,524,173 B2 * 9/2013 Yamanaka et al. ............ 422/544

2009/0269579 A1   10/2009 Minaki
2010/0294952 A1 * 11/2010 Mirkin et al. ............... 250/492.1
2010/0311059 A1 * 12/2010 Didion et al. ..................... 435/6

FOREIGN PATENT DOCUMENTS

| JP | 2005264089 | 9/2005 | |
| JP | 2006069976 | * 3/2006 | ............ C07H 23/00 |
| JP | 2008255316 | 10/2008 | |
| WO | WO 01/83155 | 11/2001 | |

OTHER PUBLICATIONS

Petersen, Svea, et. al. In Situ Bioconjugation: Sinclge Step Approach to Tailored Nanoparticle-Bioconjugates by Ultrashort Pulsed Laser Ablation, Adv. Funt. Mater. 19: 1167-1172 (2009)).*
Amendola et al. Controlled size manipulation of free gold nanoparticles by laser irradiation and their facile bioconjugation. Journal of Materials Chemistry 17: 4705-4710 (2007).*
Amendola, V., et al., "Controlled size manipulation of free gold nanoparticles by laser irradiation and their facile biconjunction", *Journal of Materials Chemistry*, Royal Society of Chemistry UK, Nov. 28, 2007, Bd. 17, Nr. 44, p. 4705-4710.
Petersen, S. et al., "In situ bioconjunction: single step approach to tailored nanoparticles-bioconjugates by ultrashort pulsed laser ablation", *Advanced Functional Materials*, Wiley-VCH, Verlag GmbH Germany, Apr. 23, 2009, Bd. 19, Nr. 8.
Slocik, J.M. et al., "Synthesis of gold nanoparticles using multifunctional peptides", *Small*, Wiley-VCH, Nov. 2005, Bd. 1, Nr. 11.
Petersen, Svea, et. al., "In situ bioconjugation—Novel laser based approach to pure nanoparticles-conjugates", *Applied Surface Science*, 2009, 253, 5435-5438.
Petersen, Svea, et. al., "In Situ Bioconjugations Sinclge Step Approach to Tailored Nanoparticie-Bioconjugates by Ultrashort Pulsed Laser Ablation", *Adv. Funt. Mater.*, 2009, 19, 1167-1172.

* cited by examiner

*Primary Examiner* — Gail R Gabel
(74) *Attorney, Agent, or Firm* — Greer, Burns & Crain, Ltd.

(57) ABSTRACT

The invention relates to a method and to a device for producing conjugates comprising or consisting of a metallic nanoparticulate component and an organic component. Said method enables activated or reactive nanoparticles containing metal to be produced by irradiating a metal body with a laser beam and prevents the modification and damage of organic components of said conjugates by laser irradiation. Said nanoparticulate metallic component comprises plasmon resonant metal. According to the invention, the claimed method of production enables particles having a metal centre and a metal-oxide covering to be produced, in particular when using a carrier fluid containing oxygen, e.g. alcohol or water.

12 Claims, 3 Drawing Sheets

```
                        SEQUENCE LISTING

<160> NUMBER OF SEQ ID NOS: 9

<210> SEQ ID NO 1
<211> LENGTH: 39
<212> TYPE: DNA
<213> ORGANISM: Artificial Sequence
<220> FEATURE:
<223> OTHER INFORMATION: SEQ ID NO 1: Oligonucleotide with specificity
      for the Y chromosome

<400> SEQUENCE: 1
tctgtgagac gacgcaccgg tcgcaggttt tgtctcaca                             39

<210> SEQ ID NO 2
<211> LENGTH: 17
<212> TYPE: DNA
<213> ORGANISM: Artificial Sequence
<220> FEATURE:
<223> OTHER INFORMATION: SEQ ID NO 2: Oligonucleotide with specificity
      for the Y chromosome

<400> SEQUENCE: 2
agagactgtg gaaccgg                                                    17

<210> SEQ ID NO 3
<211> LENGTH: 18
<212> TYPE: DNA
<213> ORGANISM: Artificial Sequence
<220> FEATURE:
<223> OTHER INFORMATION: SEQ ID NO 3: Oligonucleotide with specificity
      for the Y chromosome

<400> SEQUENCE: 3
ggcgactgtg caagcaga                                                   18

<210> SEQ ID NO 4
<211> LENGTH: 18
<212> TYPE: DNA
<213> ORGANISM: Artificial Sequence
<220> FEATURE:
<223> OTHER INFORMATION: SEQ ID NO 4: Oligonucleotide with specificity
      for the Y chromosome

<400> SEQUENCE: 4
agcacatctc ggtccctg                                                   18
```

```
<210> SEQ ID NO 5
<211> LENGTH: 56
<212> TYPE: DNA
<213> ORGANISM: Artificial Sequence
<220> FEATURE:
<223> OTHER INFORMATION: SEQ ID NO 5: Oligonucleotide with specificity
      for the Y chromosome

<400> SEQUENCE: 5
gggagggcga ugcggaucag ccauguuuac gucacuccuu gucaauccuc aucggc        56

<210> SEQ ID NO 6
<211> LENGTH: 19
<212> TYPE: DNA
<213> ORGANISM: Artificial Sequence
<220> FEATURE:
<223> OTHER INFORMATION: SEQ ID NO 6: siRNA directed against GFP

<400> SEQUENCE: 6
accuucaggg ucagcuugc                                                 19

<210> SEQ ID NO 7
<211> LENGTH: 16
<212> TYPE: PRT
<213> ORGANISM: Artificial Sequence
<220> FEATURE:
<223> OTHER INFORMATION: SEQ ID NO 7: organic component for penetration
      enhancement

<400> SEQUENCE: 7

Arg Gln Ile Lys Ile Trp Phe Gln Asn Arg Arg Met Lys Trp Lys Lys
1               5                   10                  15

<210> SEQ ID NO 8
<211> LENGTH: 14
<212> TYPE: PRT
<213> ORGANISM: Artificial Sequence
<220> FEATURE:
<223> OTHER INFORMATION: SEQ ID NO 8: organic component for penetration
      enhancement

<400> SEQUENCE: 8

Gly Arg Lys Lys Lys Arg Arg Gln Arg Arg Pro Pro Gln
1               5                   10

<210> SEQ ID NO 9
<211> LENGTH: 24
<212> TYPE: PRT
<213> ORGANISM: Artificial Sequence
<220> FEATURE:
<223> OTHER INFORMATION: SEQ ID NO 9: organic component for penetration
      enhancement

<400> SEQUENCE: 9

Tyr Gly Arg Lys Lys Arg Arg Gln Arg Arg Gly Tyr Gly Arg Lys
1               5                   10                  15

Lys Arg Arg Gln Arg Arg Arg Gly
            20
```

METHOD AND DEVICE FOR PRODUCING METAL-CONTAINING ORGANIC COMPOUNDS

The present invention relates to devices, and methods that can be carried out using said devices, for producing metal-containing compounds, which comprise or consist of a metallic nanoparticulate component and an organic component. The organic component preferably has an affinity to an analyte, in particular to a cell component. Alternatively, the organic component can be a natural or synthetic organic molecule, in particular a monomer or polymer.

OBJECT OF THE INVENTION

The object of the present invention is to provide a method, and a device suitable for carrying out the method, for producing metal-containing conjugates.

GENERAL DESCRIPTION OF THE INVENTION

The present invention achieves said object using the method and the device defined in the claims. Therein the present invention provides a method for producing, preferably for continuously producing, conjugates that comprise or consist of a metallic nanoparticulate component and an organic component. The method makes use of the production of activated or reactive nanoparticles containing metal through irradiation of a metal body with laser radiation, and avoids modification and damage of organic components of such conjugates due to laser irradiation, respectively.

The nanoparticulate metallic component preferably comprises or consists of plasmon-resonant metals, in particular Au, Ag, Ti, and/or Cu. The nanoparticulate metallic component of the compound produced using the method of the present invention is preferably present in metallic form, in particular being selected from the group comprising gold, silver, titanium, platinum, iridium, tantalum, iron, nickel, cobalt, and copper, and mixtures thereof, in particular iron-nickel alloys and cobalt-samarium alloys, gold-silver alloys (AuAg), iron-gold alloys (FeAu), and nickel-titanium alloys (NiTi), or is present as a metal oxide, in particular being selected from the group comprising the oxides of titanium, zinc, and iron, in particular ferromagnetic metal oxides thereof. Furthermore, it is preferred that the nanoparticulate metallic component be a core-sheath particle whose core is metallic and whose sheath is the oxide of the same metal, e.g. Zn (core)/ZnO (sheath). It has turned out that the method of production according to the present invention produces particles having a metallic core and a metal-oxide sheath, in particular when a carrier fluid is used that contains oxygen, e.g. alcohol or water.

For the stability of the binding of the metal-containing component with the organic component of conjugates, it is preferred that one of these components be a soft Lewis base while the other is a soft Lewis acid, or that one of these components be a hard Lewis base while the other is a hard Lewis acid, e.g. Au with an organic component containing thiol groups, or Fe with an organic component containing amine groups.

The bond between the nanoparticulate metallic component and the organic component is preferably a direct bond; optionally, the organic component can comprise what is known as a spacer group, e.g. a C1 to C6 alkyl, or a polyglycol, in particular hexaethylene glycol, the spacer group binding to the metallic component.

The organic component of the metal-containing organic compound is a Lewis base and can comprise a reaction-capable group, selected for example from C—C double bonds, in particular ethylenically-unsaturated double bonds, carboxy, carbonyl, thiol, sulfide, and epoxy groups, in particular having a terminal thiol group such as a cysteine moiety, an alkylthiol moiety or ethylene glycolthiol, or a disulfide, e.g. a pyridyl disulfide, a C1 to C12 alkyl disulfide, an ethylene glycol disulfide, or lipoic acid.

In a preferred embodiment, the organic component comprises a nucleic acid sequence and/or an amino acid sequence having a specific affinity to an analyte, in particular a specific affinity to an intracellular or extracellular cell component of a prokaryotic or eukaryotic cell, in particular an animal cell. Preferably, the organic component comprises a nucleic acid sequence, also called an oligonucleotide, that is e.g. reverse complementary to, i.e. hybridizable to a target sequence that is the analyte. Particularly preferably, the organic component is a nucleic acid sequence that is specific for a sex-chromosome-specific section of an animal cell, in particular a sperm cell.

In a further specific embodiment, the organic component comprises the antigen-binding components of an antibody, for example one or more amino acid chains that form a paratope of an antibody, in particular a natural or synthetic antibody, or an antigen-binding portion of an antibody.

Correspondingly, the organic component can be a binding portion of the compound according to the invention, e.g. a natural or synthetic, single-chain or two-chain antibody, in particular a nucleic acid sequence indicated in the present case in 5' to 3', for example RNA, DNA, phosphorylated DNA (PSNA), peptidyl-DNA, e.g. LNA (locked nucleic acid) or PNA, or a ligand specific for a receptor, e.g. for a cellular receptor, or some other compound that enters into specific interaction with a surface-bound component of a cell or a cell-internal component, in particular an antibody.

A nucleic acid sequence that is the organic component of a conjugate according to the invention can comprise for example a sex-chromosome-specific nucleic acid sequence, an allele-specific nucleic acid sequence, or an SNP-specific nucleic acid sequence.

Preferred nucleic acid sequences are TCT GTG AGA CGA CGC ACC GGT CGC AGG TTT TGT CTC ACA (SEQ ID NO. 1), the sequence AGA GAC TGT GGA ACC GG (SEQ ID NO. 2), which is specific for the bovine Y chromosome, GGC GAC TGT GCA AGC AGA (SEQ ID NO. 3), or AGC ACA TCT CGG TCC CTG (SEQ ID NO. 4), or an expression cassette that encodes a marker gene, e.g. a luminescent protein, in particular GFP, eGFP, Red, a sequence specific for a disease marker, e.g. GGG AGG GCG AUG CGG AUC AGC CAU GUU UAC GUC ACU CCU UGU CAA UCC UCA UCG GC (SEQ ID NO. 5), which is specific for the prostate membrane antigen, or a sequence that encodes siRNA, e.g. ACC UUC AGG GUC AGC UUG C (SEQ ID NO. 6), the siRNA directed against GFP.

For organic components of conjugates according to the invention that have a specific affinity to an analyte, the conjugates according to the present invention are also referred to as detection conjugates.

It is preferred that conjugates according to the invention, in particular detection conjugates, in which a metal-containing nanoparticle is bound to an organic component that has a specific affinity for an analyte, also comprise bound penetration-enhancing compounds, for example polyarginine peptides, in particular preferably having a bound myristic acid group and/or a transfection agent, selected for example from the group comprising Eugene, Lipofectamine, Oligofectamine, Optifect, DMRIE-C, AntHD, penetratin (SEQ ID NO. 7, RQIKIWFQNRRMKWKK), penetratin 43-58, HIV-1 Tat protein (SEQ ID NO. 8, GRKKKRRQRRRPPQ), Tat peptide 49-59, Tat peptide 48-62, Tat peptide 2-4, peptides containing or consisting of the sequence having SEQ ID NO. 9 (YGRKKRRQRRRGYGRKKRRQRRRG), amphipathic peptides (MAPs), e.g. the amino acid sequence KALA or KLAL, peptides containing cis-γ-amino-L-proline, VP22, LL37, TP10, MPG, galparan, transportan, MPG, SynB1, Fushi tarazu, Engrailed, pVEC, plsl, cysteine, glycine, Hoechst 33342, polysaccharides, in particular dextrane, glucosamine glycans, in particular hyaluronic acid, heparine and chitosan, lipids, polyvinylpyrrolidone, ethylene glycol, and mixtures and conjugates thereof. Alternatively or in addition, the conjugates for the enhancement of the penetration into cells can be formulated as liposomes or can be formulated in admixture with liposomes.

Furthermore, the invention relates to the use of detection conjugates and the use of the method of producing detection conjugates that comprise an organic component that is specific for an analyte, for flow cytometric analysis and/or for flow cytometric sorting of the analyte. Preferably, the analyte is bound to a particle; in particular, the analyte is a cell component. The sorting can therefore also be the sorting of cells.

In general, the present invention relates to the use of detection conjugates and to the use of the method for producing detection conjugates for analysis, optionally coupled with the subsequent step of sorting of analytes by:
excitation of the metallic nanoparticulate component of the conjugate, e.g. through incidence of radiation having an excitation wavelength that is specific for the excitation of the surface plasmon resonance,
detection of the signal emitted by the conjugate by measuring the emitted radiation, and determination of the shift of the emission or absorption maximum.

Optionally, analytes, or particles comprising the analyte, can subsequently be sorted into two or more fractions corresponding to the determined shift of the emission or absorption maximum, for example into a fraction having a signal intensity falling on one side of a threshold value, for whose analyte the organic component of the conjugate, in particular the nucleic acid sequence of the conjugate, is specific, in particular hybridizable, and a fraction for which signal intensities were measured on the other side of the threshold value, at which for example the nucleic acid sequence of the conjugate does not hybridize.

In general, the excitation wavelength can be in the range from 350 to 1000 nm, preferably in the range from 450 to 800 nm, particularly preferably 633, 488, 514, or 543 nm.

In particular, the present invention relates to the use of detection conjugates and to the use of the method for producing detection conjugates comprising a sex-chromosome-specific binding portion, in particular a sex-chromosome-specific nucleic acid sequence, for the sex-chromosome-specific detection of spermatozoa, in particular the use of detection conjugates and the use of the method for producing detection conjugates for the sorting of intact, viable spermatozoa of a male nonhuman mammal into an essentially X chromosome-containing fraction and an essentially Y chromosome-containing fraction.

In this embodiment, the invention also relates to the use of conjugates that comprise a metallic nanoparticulate component and an organic component in a method for producing a fraction of nonhuman spermatozoa by sorting using a flow cytometer, comprising the steps: contacting of intact, viable spermatozoa obtained from a male nonhuman mammal, comprising the steps of:
making single of the spermatozoa, either in drops of a sheath fluid that is preferably electrically conductive and isotonic, or in a fluid stream that is produced for example in a flow cytometer,
excitation of the metallic nanoparticulate component of the conjugate, e.g. through irradiation using radiation having an excitation wavelength that is specific for the excitation of the surface plasmon resonance,
detection of the signal emitted by the conjugate by measuring the emitted radiation,
determination of the shift of the emission maximum or absorption maximum,
sorting of the spermatozoa according to the measured signal intensity into at least two fractions of the spermatozoa, in order to produce at least two fractions of spermatozoa, for example a fraction having a signal intensity that falls on one side of a threshold value for the sex-chromosome-specific spermatozoa fraction for whose sex chromosome the organic component of the conjugate, in particular the nucleic acid sequence of the conjugate, was specific, in particular hybridizable, and a fraction of spermatozoa for which signal intensities were measured that fall on the other side of the threshold value, for which e.g. the nucleic acid sequence of fife conjugate correspondingly does not hybridize.

The excitation wavelength is in the range from 350 to 1000 nm, preferably in the range from 520 to 800 nm, e.g. for gold particles. In general, the detection of the signal emitted by the conjugate can take place by measuring scattered light; the determination of the emission maximum or absorption maximum can be the determination of the shift of the maximum of the emission wavelength, because the emitted wavelength is shifted through binding of the conjugate to an analyte.

In this use, it is particularly advantageous that in response to corresponding excitation the produced conjugates each emit a detectable signal that is qualitatively significantly different specifically for the sex chromosome contained in a spermatozoon, the signal deviating significantly depending on the hybridization, and this deviation being sufficiently large that it can be measured without a specific orientation of the spermatozoa relative to the irradiated excitation energy or relative to the detector for receiving the emitted signal.

Correspondingly, this use of the method for producing conjugates can be carried out in the production of sex-chromosome-specific spermatozoa fractions, preferably with individualizing of the spermatozoa during the detection of a signal emitted by the conjugate and during the subsequent sorting into fractions on the basis of the measured detection signal, even without orienting spermatozoa along their longitudinal axis, e.g. in a flow cytometer with the production of a continuous liquid phase or with the production of a stream of drops wherein exactly one spermatozoon is contained in each drop.

Preferably, the use in the production of a sperm fraction relates to the allocation of individualized spermatozoa to a fraction, following the detection of the signal of the detection conjugate, for example by deflecting drops or volume sections of the sheath or carrier fluid that contain a spermatozoon. The deflection can for example take place using an electrical field produced in dependence from the detected signal. Alternatively to this sorting into at least two fractions, in the use according to the invention it is also possible to leave the spermatozoa made single in the carrier medium or in the sheath fluid after detection in dependence on the level of the detection signal, or, dependent on the detection signal, to deactivate a portion of the spermatozoa that exceeded or fell below a signal threshold value during the preceding detection, the deactivation taking place for example by heating via targeted laser irradiation of the spermatozoa. In this variant of the use of conjugates, a spermatozoa fraction produced contains the non-deactivated, i.e. for example non-irradiated, spermatozoa, and the other fraction contains deactivated (not capable of fertilization) spermatozoa, the deactivation taking place in dependence on the falling below or exceeding of a threshold value for the measured detection signal. This use can therefore relate to a method in which, in a flow cytometer, a laser is used for the deactivating irradiation of individual cells in the continuous liquid stream in dependence on the signal emitted by the detection conjugate.

A preferred nucleic acid sequence that is specific for the Y chromosome of cattle in particular is SEQ ID NO. 4 (5' AGC ACA TCT CGG TCC CTG 3'); alternatively, a nucleic acid sequence of SEQ ID NO. 4 and/or NO. 5 can be used.

Alternatively to the sex-chromosome-specific nucleic acid sequence, a conjugate according to the invention can for example contain a nucleic acid sequence that is specific for an allele or for an SNP (single nucleotide polymorphism), in order to fractionate cells, in particular spermatozoa, in an allele-specific or SNP-specific fashion.

It is preferable that detection conjugates consist of colloidal gold nanoparticles having sex-chromosome-specific nucleic acid sequences bound immediately thereto, optionally additionally having penetration-enhancing compounds bound immediately to the gold nanoparticle. The detection conjugates therefore comprise the sex-chromosome-specific nucleic acid sequence in immediate binding to colloidal metal nanoparticles, in particular colloidal gold nanoparticles, and optionally additionally comprise penetration-enhancing compounds bound immediately to the nanoparticles.

For the excitation of the detection conjugates that comprise a colloidal gold nanoparticle, in the use for the fractionation of spermatozoa for example light having a wavelength of 350 to 1000 nm, preferably 450 to 1000 nm, particularly preferably approximately 800 nm, can be used for the irradiation. As a signal for the sex-chromosome-specific detection, the absorption of the excitation radiation can be measured; preferably, the sex-chromosome-specific hybridization of the nucleic acid sequence of a conjugate is detected as a change in the absorption, optionally through a shifting of the wavelength, in particular towards higher wavelengths.

On the basis of the detection of the radiation emitted by the conjugate in the use for detection of an analyte, optionally with subsequent sorting in dependence on the detected signal of the conjugate as a change in luminescence, absorption, and/or scatter, optionally with determination of the wavelength shift, the invention enables the use of the conjugate for analytical and sorting methods for cells, in particular for spermatozoa, having the steps of contactless detection of the sex-chromosome-specific hybridization and subsequent fractionation and/or deactivation of spermatozoa which are made single, in dependence on the detected signal.

The method according to the invention provides the ablation of a metal body in a carrier fluid by laser irradiation, the carrier fluid being moved, e.g. pumped, over the surface of the metal body during the laser irradiation thereof. Metal-containing nanoparticles produced by the laser irradiation are moved out of the area of the laser beam by the forced movement of the carrier fluid, so that after contacting or reaction with a precursor compound of the organic component, metal-containing nanoparticles essentially do not move through the laser beam. For the purposes of the invention, the term "metal body" comprises, in addition to one-piece metal or metal oxide, particulate metal or metal oxide, in particular metal powder or metal oxide powder, that is optionally solidified and/or can contain a binding agent.

The carrier fluid utilized in the production method is preferably a liquid, selected for example from the group comprising aqueous compositions, in particular pure, salt-free water, aqueous buffers with Tris, HEPES, MES, imidazole, glycine and/or triethanolamine, water, or such aqueous buffers containing an organic solvent, selected for example from the group comprising C1 to C5 alcohols, in particular ethanol, propanol, butanol, acetone, formaldehyde, and THF, and mixtures of at least two of these. Alternatively, the carrier fluid can be selected from the group of the above-named organic solvents and mixtures thereof; preferably, the carrier fluid is THF or acetone.

Temporally before or after the action of the laser radiation on the metal body, a precursor compound of an organic component of the conjugate is added to the carrier fluid. The precursor compound contained in the carrier fluid readily forms bonds with the metal-containing nanoparticles produced by laser irradiation of the metal body, so that the conjugates are produced for example even without reactive bifunctional coupling reagents. Preferably, the precursor compounds have at least one group that is reactive with the metal-containing nanoparticles within a short time (in particular within 0.5 μs to 100 ms) after the production of said nanoparticles by laser irradiation.

In an alternative specific embodiment, the laser radiation is ultrashort pulse laser radiation. It has turned out that the alteration of conjugates by the laser radiation is avoided through the use of ultrashort pulse laser irradiation, while irradiation of a metal body produces a sufficient quantity of nanoparticles that react with organic precursor compound in the carrier fluid to form a conjugate. At present, the avoidance of changes in produced conjugates in a production method using ultrashort pulse laser radiation is attributed to a conduct of the process in which the pulse duration, which is for example shorter than 1 to 100 ps, is shorter than the relaxation time of the metal-containing nanoparticle. Correspondingly, this embodiment can omit the generation of a movement of the carrier fluid over the metal body.

In this embodiment, the detection conjugates, which preferably are colloidal gold nanoparticles conjugated with a sex-chromosome-specific oligonucleotide, in particular PNA, are produced in that, using an ultrashort pulse laser, nanoparticles are ablated from gold in an aqueous medium as a carrier fluid, and the nucleic acid sequence is present in the aqueous medium, and penetration-enhancing agent is optionally additionally present concurrently or is added later. The production of the gold nanoparticles through laser ablation using ultrashort pulses produces nanoparticles having a reactive surface that can also comprise partially oxidized Au+, Au3+ on the surface. Surprisingly, it was found that the production of metal nanoparticles through ultrashort pulse laser ablation in the presence of the sex-chromosome-specific nucleic acid sequence, as well as optionally the presence of penetration-enhancing agents in admixture or added later, by itself brings about an immediate binding of the nucleic acid sequence or of the penetration-enhancing agent to the gold nanoparticle. Through the ultrashort pulse laser ablation, the metal particles, in particular gold nanoparticles, are partially oxidized and act as electron acceptors that form a bond with binding portions, in particular nucleic acid sequences, and with penetration-enhancing agents that are optionally present concurrently or later, said bond being e.g. a complex or coordinative bond, so that the metal is present in the conjugate in metallic form, in particular not as a metal oxide.

In order to increase the binding strength, nucleic acid sequences, or the penetration-enhancing agent (the penetration-enhancing compound), can be provided with groups that are reactive with gold, in particular with thiol, carboxy, amide, and/or amine groups at the 3' and/or 5' end, preferably at the 3' end of nucleic acid sequences, for binding to a nanoparticle. It is possible to carry out this production method continuously in a flow chamber; wherein aqueous medium containing nucleic acid sequence is made to flow over the gold, while colloidal nanoparticles are produced from the gold by irradiation with ultrashort pulse laser radiation. In this embodiment, penetration-enhancing agents can be used in mixture with nucleic acid sequences in a desired ratio, or penetration-enhancing agents can be added to the fluid stream downstream from the location of the production of the colloidal gold nanoparticles, so that after the reaction of the nanoparticles with nucleic acid sequences, reactive locations on the nanoparticles can react with penetration-enhancing agent.

According to the invention, magnetic nanoparticles are produced, e.g. nanoparticles containing or consisting of Fe, Fe oxide, and/or an Fe alloy, which are then detectable through detection of the shift of the relaxation when there is coupling to the specific sex chromosome, e.g. through detection of the relaxation difference due to the specific binding of the detection conjugate to or in mammalian spermatozoa, e.g. the relaxation difference between spermatozoa containing X chromosomes in comparison to spermatozoa containing Y chromosomes given a sex-chromosome-specific nucleic acid sequence for subsequent selection of the spermatozoa. Given an unspecific nucleic acid sequence of the detection conjugate, the detection and selection can take place on the basis of the quantitative relaxation difference, because spermatozoa also differ by the difference in total DNA content.

Alternatively to the sex-chromosome-specific nucleic acid sequence, it is therefore possible for an accidental or random nucleic acid sequence, and/or a DNA-intercalating substance e.g. a dye, in particular Hoechst Bisbenzimid 33342, to be contained in the detection conjugates as an organic component, so that for identification on the basis of the sex chromosome a quantitative difference of the signal can be detected due to the lower total DNA content of the Y chromosome-containing spermatozoa.

The nanoparticles contained in detection conjugates according to the invention are preferably produced through ultrashort pulse laser ablation of a metal in an aqueous medium, e.g. immersed in an aqueous composition, the ultrashort pulse having a pulse duration of 10 fs to 15 ps, at a wavelength of greater than 330 nm, maximally 1030 nm, in particular in the range from 500 to 1000 nm. The duration of the ablation is preferably approximately 10 to 200 s, e.g. 40 to 60 s, in particular 53 s, at a pulse energy of approximately 50 to 200 µJ, in particular 80 to 120 µJ, preferably 120 µJ, and the pulse duration is approximately 100 to 140 fs, in particular approximately 120 fs, preferably at 800 nm.

The production method according to the present invention yields nanoparticles that, even with the bound binding portion, which is for example a peptide or a sex-chromosome-specific nucleic acid sequence, preferably as ANA, have a size and/or conformation that is particularly suitable for penetration of the cell wall of mammalian spermatozoa, in particular of cattle. The nanoparticles have for example a size of 1 to 150 nm, up to 100 nm, preferably 5 to 50 nm or up to 25 nm.

In this embodiment, due to the production of nanoparticles using ultrashort pulse laser radiation with low thermal impact on components of the conjugates or on the carrier fluid, the method for producing detection conjugates containing nanoparticles produces detection conjugates in a very short time span, e.g. from 1 to 10 ps; within which, there is a high reactivity of the metallic nanoparticles. The nanoparticles have this reactivity immediately after they are produced, for example with nucleic acid sequences containing thiol, while the agglomeration of the nanoparticles begins subsequent to this time span. The low thermal impact is advantageous because it reduces damage to the organic components, and preferably essentially prevents such damage. Correspondingly, the nucleic acid sequences that are to be used for the production method preferably comprise thiol, keto, carboxy, amide, or amine groups or phosphine groups, in order to produce a corresponding coordinative bond to the gold nanoparticles, i.e. without using an additional coupling reagent between the nucleic acid sequence and the nanoparticle, so that for example the detection conjugate consists of metallic nanoparticle and nucleic acid sequence comprising a reactive group, in particular at an end position, for example a thiol, keto, carboxy, amide, or amine group, or a phosphine group, that has formed a coordinative bond with the nanoparticle.

In a preferred embodiment, the method for producing conjugates having a metallic nanoparticulate component and an organic component provides that a carrier fluid, in which particular is a carrier liquid, be moved over the surface of a metal by a circulation device or pumping device, and that the metal be irradiated using a laser. Metallic nanoparticles are produced by the laser irradiation of the metal. The carrier fluid can comprise a precursor compound of the organic component of the conjugate, or this precursor compound can be added to the carrier fluid downstream from the metal.

Due to the movement of the carrier fluid over the surface of the metal during the irradiation with laser radiation, produced nanoparticles are moved out of the immediate region of the laser beam, and dependent on the repetition rate of the laser, are excited to a reduced degree or are no longer excited by the laser beam. Preferably, therefore, in this embodiment the laser radiation dependent on its repetition rate, essentially has a reduced effect or no effect on organic components of conjugates formed already, which comprise an organic component bound to the metallic component. This has the advantage that precursor compound contained in the carrier fluid can react with the reactive nanoparticles immediately subsequent to the production of said nanoparticles by laser irradiation, but, due to the movement of the carrier fluid, said reaction takes place outside the volume section of the carrier fluid which is crossed by the laser beam.

It has turned out that in the production of nanoparticles from a metallic surface using continuous laser irradiation in a carrier fluid that contains precursor compound, when there is movement of the carrier fluid over the surface of the metal the produced conjugates are produced in a higher yield than is the case using an ultrashort pulse laser, and/or said conjugates show no changes in the precursor compound, with the exception of the reactive groups of the precursor compound that form a bond with the nanoparticles, for example thiol, keto, carboxy, and amide groups. Thus, for example for oligonucleotides it could be shown that by the conduct of the process according to the invention with movement of the carrier fluid over the surface of the metal during the laser irradiation, if the carrier fluid already contains precursor compound upstream from the surface of the metal, essentially no changes occur in the oligonucleotide, with the exception of the bond to the nanoparticle. In contrast thereto, when nanoparticles were produced using high laser energy with a static conduct of the process, i.e. without movement of the carrier fluid, chemical changes were detected in the organic component of conjugates, and at present it is assumed that these changes are due to the laser irradiation of conjugates.

It is preferable that the carrier fluid be moved by pumping the carrier fluid in the container in which the metal is situated and can be irradiated by a continuously radiating laser. In a simple embodiment, the pumping can be produced by an agitator as a pumping device inside the container, the container being supplied batchwise with carrier fluid containing precursor compound, and a metal or metal oxide situated in the carrier fluid being irradiated with continuous laser radiation during agitation. Alternatively, the circulation device can be a circulation device connected to the container that comprises a pumping device for moving the carrier fluid. Preferably, the container has an inlet for precursor compound and/or an outlet opening.

In the description, the term "precursor compound" comprises both precursor compounds and precursor substances .for the organic components of a conjugate according to the invention, in particular an organic component that is specific for an analyte, as well as unspecific organic precursor compounds and substances, such as precursor compounds of penetration-enhancing or unspecific organic compounds.

In the description of the method according to the invention for producing conjugates, descriptions of method steps are also to be considered as establishing the adaptation of corresponding elements of a device suitable for the method, for each described method step.

In a preferred embodiment, the carrier fluid is pumped, using a pump or a pressurized liquid source, through a first inlet opening into a flow cell in which the metal is fixed and irradiated by a laser beam, and the fluid subsequently exits the flow cell through an outlet opening.

Particularly preferably, the metal forms a section of the inner surface of the flow cell, and is for example situated on an inner surface of the flow cell. The flow cell preferably has a passage cross-section adjacent to the surface of the metal of a maximum of 7 $cm^2$, preferably a maximum of 2 $cm^2$, more preferably a maximum of 1 $cm^2$, more preferably a maximum of 1 to 50 $mm^2$ or up to 20 $mm^2$, so that carrier fluid moves past the metal surface only at a limited distance therefrom, and precursor compound contained in the carrier fluid, or precursor compound added to the carrier fluid following the laser irradiation of the metal, i.e. added downstream from the laser beam or from the metal, is present only in a limited volume section adjacent to the metal surface and reacts there with the produced nanoparticles, while at a greater distance from the metal surface, in which no nanoparticles are present immediately after the laser irradiation of the metal surface, essentially no carrier fluid and no precursor compound are present.

The laser beam directed onto the surface of the metal in the container or flow channel is preferably produced by a laser and passes through a wall section of the container or of the flow chamber that is transparent to the laser radiation. Preferably, the flow chamber has a height over the metal body of from 100 µm to 4 mm, so that carrier fluid can flow over the metal body in a layer that is 100 µm to 4 mm thick. Preferably, the chamber is essentially situated vertically, or is oriented in the vertical direction for the flowing through, the laser beam being directed onto a surface of the metal body that is essentially oriented vertically. The laser beam can be directed approximately horizontally onto the surface of the metal body.

Due to the movement according to the present invention of the carrier fluid over the surface of the metal during the laser irradiation of the metal, nanoparticles produced by the laser irradiation are moved out of the volume section of the container or of the flow channel crossed by the laser beam. As a consequence, it is possible for the laser radiation to be ultrashort pulse laser radiation or continuous laser radiation produced for example by a CW laser, a solid-state laser, e.g. an Nd:YAG laser, an erbium:YAG laser, a Ti:sapphire laser, or a fiber or diode laser.

It is preferable that the laser radiation impinging on the metal or metal oxide surface is moved relative to the metal body. The movement of the laser radiation relative to the metal body can take place through a spiral-shaped or meandering guidance of the laser beam over the metal or metal oxide surface, or by a movement of this sort of the chamber given a stationary orientation of the laser radiation.

In order to produce a movement of the laser beam relative to the surface of the metal, the metal body or the flow chamber can be fixed on a movable fixing device, and/or the laser beam can be moved over the surface of the metal, for example by moving a deflecting mirror that directs the laser beam from the laser medium onto the surface of the metal.

The carrier fluid can be cooled, preferably to a temperature above its solidification point, e.g. to a maximum of 20° C., preferably to 1 to 10 or to 5° C.; carrier fluid having or consisting of organic solvent can be cooled to below 0° C. Correspondingly, the device according to the present invention preferably comprises a cooling device for cooling the carrier fluid to these temperatures.

Preferably, during the method additional precursor compounds, for example of penetration-enhancing agents, are added downstream from the metal body.

In a further preferred specific embodiment in which carrier fluid is moved over the surface of the metal continuously, less preferably intermittently, a volume section of the flow channel downstream from the metal and/or downstream from the laser beam is acquired by a sensor. Preferably, the sensor is a spectrometer, in particular a spectrophotometer. Alternatively or in addition, a volume section upstream from the metal and/or upstream from the laser beam can be measured by a sensor, in particular by a spectrometer. The measurement values recorded by at least one spectrometer can optionally be used to control the positioning of the laser beam, to control the positioning of the metal, and/or to control the laser irradiation with regard to its intensity or its movement relative to the surface of the metal body, and in particular in the case of ultrashort pulse laser radiation these values can be used to control the frequency and/or pulse duration, e.g. by coupling the measurement values recorded by a spectrometer to a control unit that controls the movement of the fixing device for the metal, the positioning of the laser beam, and/or the production of the laser beam and/or the dosing of precursor compound.

Preferably, following the production of conjugates the method includes the step of separating at least a part of the carrier fluid, and/or the step of separating precursor compounds not converted to conjugate, or unconverted nanoparticles, from the produced conjugates, e.g. after the exiting of the carrier fluid containing conjugates through outlet opening 3. For separation of unconverted nanoparticles or precursor compound from the conjugate, conventional separating methods can be used, in particular chromatographic methods, for example size exclusion chromatography or an affinity-chromatographic separation of conjugates using a chromatography medium that comprises immobilized analyte, in particular if the first precursor compound, or the organic component of the conjugate produced therefrom, has a specific affinity to the analyte. For the separation, optionally a second chromatographic step can be carried out that is specific for the metallic component of conjugates; for example, in the case of ferromagnetic nanoparticles this can be the separation of conjugate from carrier fluid using a magnetic field, by centrifugation, and/or by AFFFF (asymmetrical flow field-flow fractionation).

DETAILED DESCRIPTION OF THE INVENTION

The present invention is now described in more detail with reference to the Figures, on the basis of examples, in which.

In the Figures, identical reference characters designate functionally identical elements.

Figure 1:
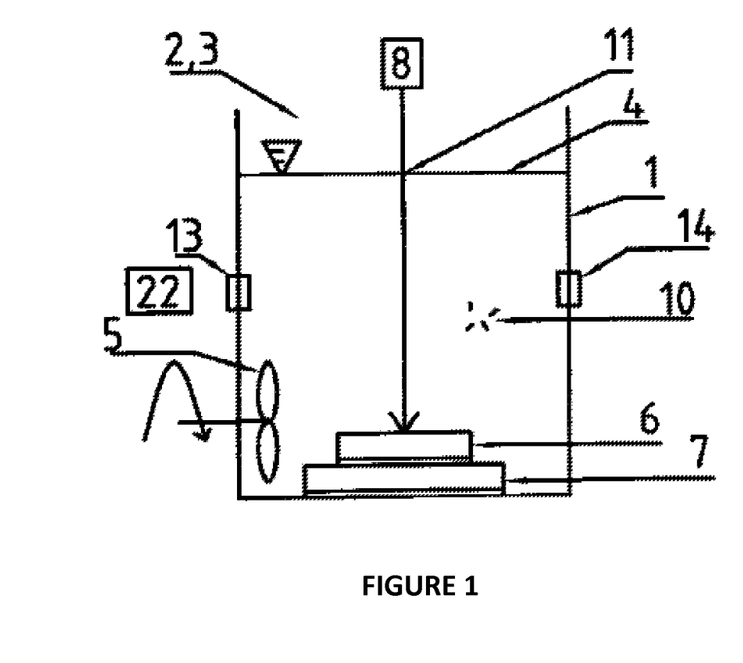
FIG. 1 shows a schematic view of a simple device for carrying out the method according to the invention.

A simple device suitable for use in the method is shown in FIG. 1, comprising a container 1 having a first inlet opening 2 and an outlet opening 3, here in the form of a common opening. For generation of a movement of the carrier fluid 4, a pumping device 5 is situated so that it is in contact with carrier fluid 4, for example inside container 1. As is shown schematically, in this specific embodiment pumping device 5 can be agitator stirrer.

The metal, in the form of a metal body 6 that comprises or consists of one-piece or particulate metal and/or metal oxide, is fixed in container 1 by a fixing device 7. Fixing device 7 can also be a container open at one side if metal body 6 is in powder form. A laser 8, comprising a laser medium in connection with optical elements for producing a laser beam, is situated such that the laser beam is directed against the section of fixing device 7 on which metal body 6 is to be situated. Preferably, the laser beam produced by laser 8 is controlled by a mirror 9, said mirror 9 being movable and controlled in order to permit a movement of the laser beam relative to the section of fixing device 7 in which metal body 6 is situated.

Alternatively or in addition, fixing device 7 can be connected to a control unit and be controlled movably in order to move its section in which metal body 6 is to be situated relative to the laser beam.

Through first inlet opening 2, a first precursor compound 10 can be added to carrier fluid 4, said precursor compound forming an organic component of the conjugate with the metallic nanoparticle produced from metal body 6 by the laser beam.

Optionally, a second and further precursor compound can be added, for example penetration-enhancing agents that, like first precursor compound 10, react with the metallic nanoparticle immediately after its production by laser irradiation to form a conjugate.

Figure 2:
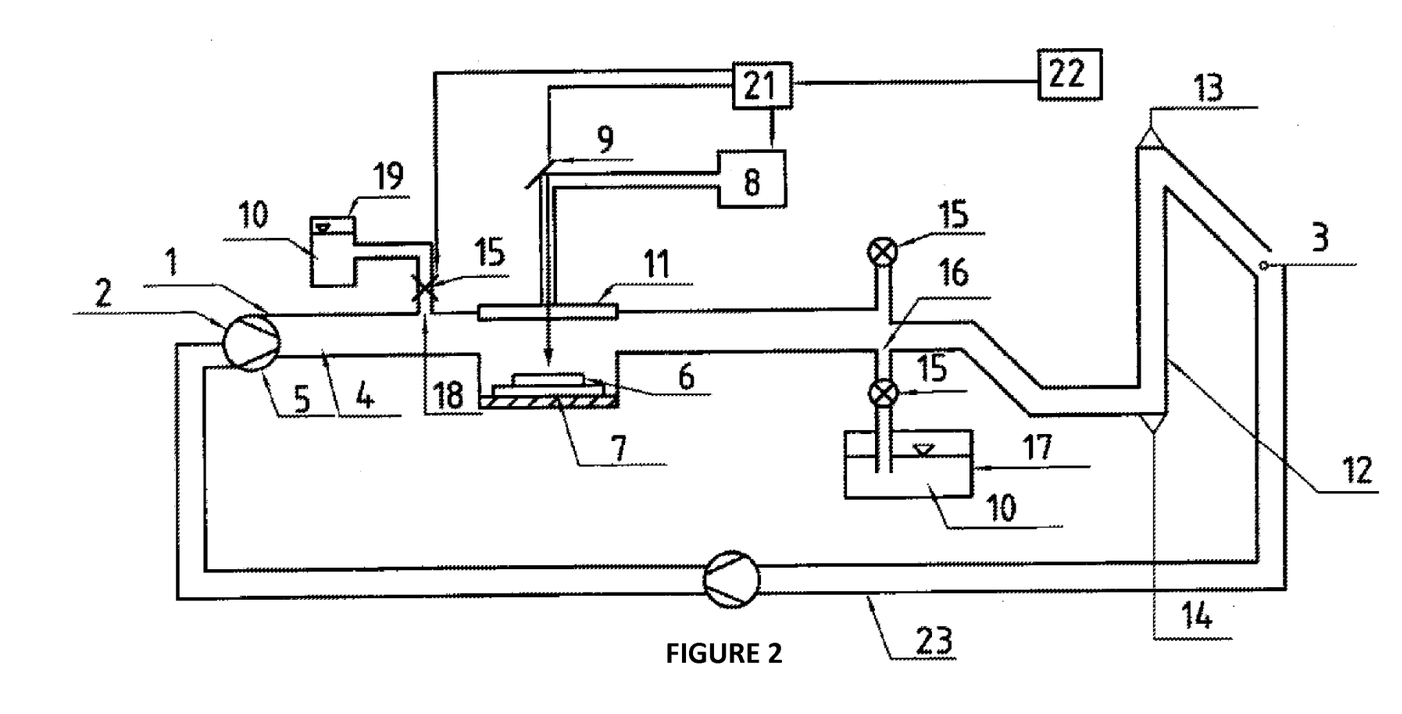
FIG. 2 shows a preferred specific embodiment of a device for carrying out the continuous method, FIG. 3 schematically shows a further specific embodiment of a device for carrying out the method of the present invention.
Figure 3:
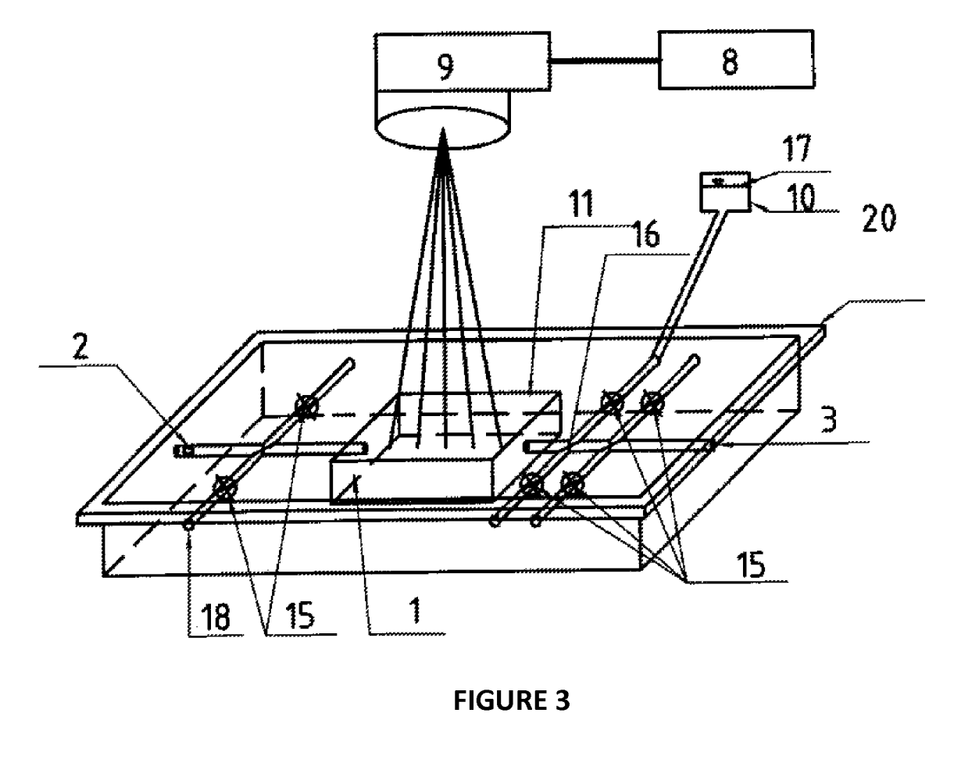

FIGS. 2 and 3 show specific embodiments in which container 1 is realized as a flow channel through which carrier fluid flows continuously or intermittently during the execution of the method. Correspondingly, the properties of the device or method named with reference to these Figures can be combined with one another and/or with the properties named in the preceding description.

FIG. 2 shows a preferred specific embodiment of a device for use in the production of devices according to the invention for use in a method for producing conjugates, in which container 1 is formed as a flow channel. Container 1 at its first end has a first inlet opening 2 and at its second end oppositely situated has an outlet opening 3. In a section of container 1, formed as a flow channel, there is situated a fixing device 7 for accommodating a metal body 6. Preferably, container 1, realized as a flow channel, is circumferentially closed, and opposite the fixing device 7 has a section 11 that is transparent to the laser radiation that is used. Correspondingly, laser 8, optionally having a mirror 9 for controlled deflection, is situated such that the laser beam is directed through the transparent section of container 1, realized as a flow channel, onto the section of fixing device 7 in which metal body 6 is to be situated. In general, first precursor compound 10 can be added to the carrier fluid before or after entry into the first inlet opening. Preferably, container I realized as a flow channel, immediately downstream from fixing device 7 has a second inlet opening 16 to which there is connected a second supply container 19 for a first precursor compound 10 and/or for a second precursor compound, e.g. a precursor compound of a penetration-enhancing agent. The connecting conduit to second inlet opening 16 preferably has a dosing device 15, also designated dosing valve 15 for the purposes of the present description.

Container 1, realized as a flow channel, can have, in addition or alternatively to second inlet openings 16, one or more third inlet openings 18 situated in a section of the flow channel between first inlet opening 2 and fixing device 7. The third inlet opening 18 is coupled to a second supply container 19 and can be controlled via a further dosing valve 15 situated in the connecting conduit between second supply container 19 and third inlet opening 18. Second supply container 19 can be filled for example with a first 10 and/or second precursor compound.

Preferably, therefore, the conduits that connect first inlet opening 2 to the first supply container for carrier fluid, and that connect a second inlet opening 16 and a third inlet opening 18 to the respectively associated second and third supply container, each have controllable dosing valves 15 that are particularly preferably connected to a control unit 21.

For the monitoring and/or controlling of the device and of the method, the device has a sensor 22 that detects a property of the substances contained in the carrier fluid. Preferably, sensor 22 is a spectrometer, in particular a spectrophotometer, whose area of detection is at least a section of the internal volume of container 1. Particularly preferably, container 1, realized as a flow channel, has, in a section between fixing device 7 and outlet opening 3, i.e. downstream from fixing device 7 or downstream from the laser beam, in which section said laser beam crosses through the internal volume of container 1, a cuvette section 12 that has a distance between two separated cuvette walls 13, 14 that is greater than the diameter of the flow channel, the detector being situated on a first cuvette wall 13 and/or on a second cuvette wall 14. First cuvette wall 13 is preferably optically transparent to a wavelength measured by the sensor, while second cuvette wall 14 can be optically transparent to a wavelength produced by a radiating element of the sensor, or to the wavelength measured by the sensor, or can be a mirror for reflecting radiation against first cuvette wall 13.

Particularly preferably, sensor 22 is connected to a control unit 211 that is set up to produce control signals in reaction to measurement values of the detector, for the control of laser 8, of the position of mirror 9, and/or of the setting of a dosing valve 15 that is used for the dosing of a first and/or second precursor compound, and for communication of said control signals is connected to laser 8, to the positioning device of mirror 9, and/or to dosing valves 15, via a data line.

In a further preferred specific embodiment, outlet opening 3 is connected to inlet opening 2 via a return conduit 23 that preferably contains a controlled pump, through which at least a portion of the carrier fluid is recirculated in controlled fashion from outlet opening 3 to inlet opening 2 When the method according to the present invention is carried out. In this specific embodiment, carrier fluid can be recycled through the section of container 1 in which the laser radiation is directed onto metal body 6 and passes through a volume section of container 1, the recirculation of at least a portion of the carrier fluid resulting in the action of the laser beam on already-produced nanoparticles. In this specific embodiment, it is preferred, in a first method step, to cause carrier fluid without precursor compound to flow through the flow channel and to irradiate metal body 6 with laser radiation, so that the recirculation of carrier fluid from outlet opening 3 to inlet opening 2 causes metallic or metal oxidic nanoparticles suspended in the carrier fluid to move through the volume section of container 1 in which the laser radiation passes through container 1. It has turned out that the action of laser radiation on already-produced nanoparticles suspended in the carrier fluid causes a targeted change in the nanoparticles, in particular a reduction in their size or size distribution, and thus for example results in smaller particles, preferably having a homogenous or a narrow size distribution. Here it is preferred, in a second method step, to introduce first 10 and/or second precursor substance into container 1, realized as a flow channel, through a second inlet opening 16, the recirculation of carrier fluid from outlet opening 3 to inlet opening 2 being stopped, and carrier fluid being made to exit through outlet opening 3, preferably with subsequent separation of at least a portion of the carrier fluid from the produced conjugates.

FIG. 3 shows a further preferred specific embodiment of the device according to the invention for use in the method for producing conjugates, in which a container 1, realized as a flow channel, is situated inside a housing 20. Laser 8 produces a continuous laser beam or a pulsed laser beam that is directed, using controllable mirror 9, through a transparent section of the wall of container 1 onto metal body 6. Mirror 9 is for example attached to an adjustment device controlled by a control unit, and forms for example a scanning device (scanner). A first inlet opening 2 of container 1, realized as a flow channel, is connected to a supply container (not shown) for carrier fluid, and carrier fluid flows to said inlet opening by means of application of pressure, produced for example by a pump 5. The carrier fluid can be mixed with precursor compound, or precursor compound can be added via second inlet openings 16 and/or third inlet openings 18, in particular if the carrier fluid contains no precursor compound when it flows into first inlet opening 2.

The conduits that connect first inlet opening 2 to a first supply container (not shown) for carrier fluid, and that connect second inlet openings 16 and third inlet openings 18 to the respectively associated second or third supply container (not shown), preferably each have controllable dosing valves 15 that are particularly preferably connected to a control unit 21, as is described with reference to FIG. 2.

The flow channel has, in a wall section, a fixing device 7 on which a metal body 6 is situated. Wall section 11 situated opposite fixing device 7 is transparent to the laser radiation.

As is shown schematically, container I can be formed by a housing 20 that can be divided at least in the section in which fixing device 7 is situated, in order for example to position metal body 6 on the fixing device.

EXAMPLE 1

Production of a Detection Conjugate Having Gold Nanoparticles

For production of a detection conjugate having a metallic nanoparticle, gold foil was introduced as a metal body into a device according to FIG. 1, in an aqueous solution as carrier liquid containing a nucleic acid sequence corresponding to SEQ ID NO. 3 as precursor compound. The gold foil was irradiated with 120 fs laser pulses at a wavelength of 800 nm at a maximum energy of 400 μJ per pulse, with beam diameter 4 mm at a distance of approximately 40 mm from the lens to the gold foil, at a repetition rate of 5 kHz. The energy applied to the gold foil was approximately 100 μJ. The aqueous solution contained approximately 3 μM in nucleic acid sequence in water, with a layer height of approximately 1 cm over the gold foil.

Analysis of the reaction products by polyacrylamide gel electrophoresis showed only a slight degradation of the nucleic acid sequence. Analysis of the reaction products by transmission electron microscopy showed that the conjugates had a size distribution having an average of approximately 5.2 to 5.5 nm. The conjugates were not agglomerated, and had an approximately spherical shape; with the parameters used, approximately 20 μg/min gold particles were produced, which entered into a stable bond with the nucleic acid sequence without the use of additional chemical coupling reagents.

When this method was repeated with application of higher energy by laser radiation, without or alternatively with movement of the aqueous solution, the same conjugates were produced; analysis of the case with movement of the aqueous solution showed a smaller proportion of conjugates having a degraded nucleic acid sequence. This shows that the movement of the carrier fluid according to the present invention permits a large amount of energy to be applied to the metal body by laser irradiation without causing a significant degradation of conjugates.

The process was also carried out in a device having a flow channel corresponding to FIG. 3; here the carrier fluid was not recycled. The second and third inlet openings were closed, and the outlet opening was connected to a collecting container by a hose. The carrier fluid pumped into first inlet opening 2 contained an oligonucleotide according to SEQ ID NO. 3 as a precursor compound, and was conveyed at a volume flow of 1 mL/min. The volume section of the flow channel between the metal body (gold foil) and the transparent wall section was approximately 2 mL.

As a laser, an ultrashort pulse laser having a radiation power of approximately 200 to 300 μJ was used.

For the purification, produced conjugates in carrier fluid were separated by centrifugation from oligonucleotides that were not bound to oligonucleotides and from nanoparticles not bound to an organic component.

EXAMPLE 2

Use of the Method for Producing Conjugates for the Detection of Sperm Cells Containing Y Chromosomes in Fresh Semen, and Sex-Specific Sorting Thereof Freshly obtained bull semen was diluted in diluent in standard fashion, and was incubated with detection conjugate that was produced according to a variant of Example 1 for 30 to 120 minutes, preferably at a temperature of 20° C. to 40° C., and was subsequently irradiated in a flow cytometer according to U.S. Pat. No. 5,125,759 or DE 10 2005 044 530 with light having the respective excitation wavelength (520 nm) for the gold nanoparticles. The emission was measured.

For the spermatozoa containing Y chromosomes specifically labeled with detection conjugate according to Example 1, a luminescence signal was measured that exhibited a maximum that was shifted in comparison to the signal that was measured for the spermatozoa containing X chromosomes. This shows that upon hybridization of the nucleic acid sequence, this detection conjugate produces a signal that is specific for the analyte when irradiated at the excitation wavelength, while cells that do not contain a sequence that hybridizes with the nucleic acid sequence of the detection conjugate under irradiation emit a signal differing therefrom.

For the spermatozoa dyed in chromosome-specific fashion with detection conjugate according to Example 1, a change in the detected surface plasmon resonance was determined for spermatozoa containing the Y chromosome, while the spermatozoa containing the X chromosome showed a surface plasmon resonance that was changed significantly less.

LIST OF REFERENCE NUMERALS 1 container
2 first inlet opening
3 outlet opening
4 carrier fluid
5 pumping device
6 metal body
7 fixing device
8 laser
9 mirror
10 first precursor compound
11 transparent section
12 cuvette section
13 first cuvette wall
14 second cuvette wall
15 dosing valve, dosing device
16 second inlet opening
17 first supply container
18 third inlet opening
19 second supply container
20 housing
21 control unit
22 sensor
23 return conduit

The invention claimed is:

1. A method for producing conjugates that comprise a metal-containing nanoparticulate component and an organic component, the method comprising:
   mixing a carrier fluid with a precursor of the organic component;
   flowing the carrier fluid with the precursor of the organic component through a flow channel and over a metal or metal oxide body situated within the flow channel in a section of the flow channel between an inlet and outlet of the flow channel, irradiating the surface of the metal or metal oxide body during said flowing using a continuous laser beam to produce metal-containing nanoparticles, wherein the carrier fluid is moved over the surface of the metal or metal oxide body by a pumping device, and the carrier fluid is moved from the inlet opening to the outlet opening permitting the precursor of the organic component to bond with the metal-containing nanoparticles and form the conjugates that comprise the metal-containing nanoparticulate component and organic component.

2. The method according to claim 1, wherein the continuous laser beam produced is by a continuous wave laser.

3. The method according to claim 1, wherein the metal or metal oxide body is one-piece or particulate metal or metal oxide.

4. The method according to claim 1, wherein the carrier fluid is moved over the surface of the metal or metal oxide body in a turbulent flow.

5. The method according to claim 1, wherein at least one additional precursor compound of an organic component is added to the carrier fluid before or after the carrier fluid is moved over the surface of the metal or metal oxide body.

6. The method according to claim 1, wherein the carrier fluid is collected at the outlet end, and the formed conjugates are separated from unconverted precursor and nanoparticles.

7. The method according to claim 1, wherein at least a portion of the carrier fluid is recirculated via a return conduit from the outlet to the inlet.

8. The method according to claim 1, further comprising a cuvette section in the flow channel between the inlet opening and outlet opening downstream of the metal or metal oxide body and detecting at least one property of the carrier fluid in the cuvette section of the flow channel and generating a measurement signal upon said detecting.

9. The method according to claim 8, wherein said detecting is a spectrometric detection or dynamic light scattering.

10. The method according to claim 8, wherein a control signal is generated in reaction to said detecting of the carrier fluid, and said control signal controls the laser beam and/or a movement of the laser beam relative to the metal or metal oxide body, and/or controls the addition of precursor compound to the carrier fluid.

11. The method according to claim 1, wherein the precursor is selected from the group consisting of oligonucleotides, peptides, polyethers, polyesters, polyamides, and monomers having at least one reactive group selected from unsaturated C—C bonds, disulfide groups, thiol groups, keto groups, carboxy groups, phosphine groups, amine groups, and amide groups.

12. The method according to claim 1, wherein the metal is gold (Au), and the precursor compound is a sex-chromosome-specific oligonucleotide.

* * * * *